United States Patent
Kamada et al.

(10) Patent No.: US 11,549,925 B2
(45) Date of Patent: Jan. 10, 2023

(54) NOX SENSOR ELEMENT AND NOX SENSOR

(71) Applicant: NGK SPARK PLUG CO., LTD., Nagoya (JP)

(72) Inventors: Kentaro Kamada, Nagoya (JP); Hitoshi Furuta, Nagoya (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 281 days.

(21) Appl. No.: 16/834,299

(22) Filed: Mar. 30, 2020

(65) Prior Publication Data
US 2020/0319156 A1 Oct. 8, 2020

(30) Foreign Application Priority Data

Apr. 8, 2019 (JP) .............................. JP2019-073294
Jan. 28, 2020 (JP) .............................. JP2020-011387

(51) Int. Cl.
*G01N 33/00* (2006.01)
*G01N 27/419* (2006.01)
*G01N 27/407* (2006.01)

(52) U.S. Cl.
CPC ..... *G01N 33/0037* (2013.01); *G01N 27/4074* (2013.01); *G01N 27/419* (2013.01)

(58) Field of Classification Search
CPC .. G01N 27/419; G01N 33/0037; G01N 27/41; G01N 27/4067; G01N 27/4074; G01N 27/4077; G01N 27/409; G01N 27/4071; G01N 27/4072; G01N 33/0054; G01N 27/4065; G01N 27/4078; G01N 27/414; G01N 27/417; G01N 27/4175; F01N 11/007; F01N 2560/026; F01N 11/00; F01N 2550/02; F01N 2560/021; F01N 2560/06; F01N 2610/02; F01N 2610/144;
(Continued)

(56) References Cited

U.S. PATENT DOCUMENTS

| | | | |
|---|---|---|---|
| 6,695,964 B1 * | 2/2004 | Ando | G01N 27/4074 73/23.31 |
| 8,826,727 B2 * | 9/2014 | Kato | G01N 27/419 73/23.31 |
| 9,518,954 B2 * | 12/2016 | Ishiguro | G01N 27/4175 |

(Continued)

FOREIGN PATENT DOCUMENTS

JP 2012-18189 A 1/2012

*Primary Examiner* — Nimeshkumar D Patel
*Assistant Examiner* — Gedeon M Kidanu
(74) *Attorney, Agent, or Firm* — Leason Ellis LLP; Melvin C. Garner; Mitsuhiro Haraguchi

(57) ABSTRACT

A NOx sensor element includes: a first pump cell configured to adjust an oxygen concentration in a first measurement chamber; a diffusion resistance portion configured to adjust a diffusion rate of a measurement target gas introduced into the first measurement chamber; and a second pump cell in which a pump current corresponding to a NOx concentration in the measurement target gas after the adjustment of the oxygen concentration, flows. The first pump cell includes: a first solid electrolyte; an inner pump electrode containing a noble metal, and exposed to the first measurement chamber; and an outer pump electrode containing a noble metal, and disposed outside the first measurement chamber. The outer pump electrode contains not less than 22% by mass of a main component of the first solid electrolyte.

10 Claims, 5 Drawing Sheets

(58) Field of Classification Search
CPC ........ F01N 3/035; F01N 3/106; F01N 3/2066; F01N 3/208
See application file for complete search history.

(56) References Cited

U.S. PATENT DOCUMENTS

| | | | | |
|---|---|---|---|---|
| 9,551,260 | B2* | 1/2017 | Kakimoto | G01N 27/419 |
| 10,684,248 | B2* | 6/2020 | Furuta | G01N 27/41 |
| 11,249,045 | B2* | 2/2022 | Nakagaki | G01N 27/419 |
| 2010/0314264 | A1* | 12/2010 | Nishijima | G01N 33/0037 |
| | | | | 205/781 |
| 2011/0048970 | A1* | 3/2011 | Sugaya | G01N 27/419 |
| | | | | 205/781 |
| 2012/0160012 | A1* | 6/2012 | Kato | G01N 27/419 |
| | | | | 73/31.05 |
| 2014/0190828 | A1* | 7/2014 | Kamada | G01N 27/4078 |
| | | | | 204/427 |
| 2018/0095051 | A1* | 4/2018 | Konno | G01N 27/41 |
| 2018/0172623 | A1* | 6/2018 | Araki | G01N 27/41 |

* cited by examiner

| PROPORTION OF COMPONENT OF FIRST SOLID ELECTROLYTE CONTAINED IN OUTER PUMP ELECTRODE (% BY MASS) | EVALUATION |
|---|---|
| 22 | ○ |
| 14 | × |

NOX SENSOR ELEMENT AND NOX SENSOR

This application claims the benefit of priority to Japanese Patent Applications No. 2019-073294 filed on Apr. 8, 2019 and No. 2020-011387 filed Jan. 28, 2020, the contents of which are incorporated herein by reference in their entirety.

FIELD OF THE INVENTION

The present invention relates to a NOx sensor element and a NOx sensor.

BACKGROUND OF THE INVENTION

In association with tightening of regulations on exhaust gas discharged from internal combustion engines of automobiles and the like, the amounts of nitrogen oxides (NOx) in such exhaust gas have been required to be reduced. Accordingly, development of NOx sensors capable of directly measuring the NOx concentration in exhaust gas has been in progress in recent years. A NOx sensor includes a NOx sensor element having a first pump cell and a second pump cell in which a pair of electrodes are formed on surfaces of a solid electrolyte having oxygen ion conductivity such as zirconia.

In the NOx sensor, the first pump cell pumps out or pumps in oxygen in a first measurement chamber that is in communication with a space for a NOx-containing measurement target gas. At this time, the oxygen concentration in the first measurement chamber is measured by an oxygen concentration detection cell, and the first pump cell is controlled such that the oxygen concentration in the first measurement chamber becomes a predetermined oxygen concentration. When constant voltage is applied to the second pump cell disposed in the first measurement chamber or a NOx measurement chamber different therefrom, NOx contained in the measurement target gas having been subjected to control (adjustment) of the oxygen concentration is decomposed into nitrogen ($N_2$) and oxygen ($O_2$). At this time, a second pump current that flows between the pair of electrodes of the second pump cell is measured, whereby the NOx concentration in the measurement target gas is detected.

In the NOx sensor having the above-described configuration, the electrodes are merely disposed on each solid electrolyte, and thus the electrodes of the NOx sensor element (detection element) are not sufficiently activated, and sufficient sensor characteristics are not obtained.

In view of this, the following technique has been proposed: in a rich atmosphere, a NOx sensor element is disposed and exposed to high temperature, and alternating voltage is applied between a pair of electrodes of a first pump cell, whereby aging treatment is performed (see Japanese Patent Application Laid-Open (kokai) No. 2012-18189).

Problems to be Solved by the Invention

Meanwhile, as shown in FIG. 6, the above-described rich aging treatment causes a part of an inner pump electrode (Ip1–electrode) 1002 of the NOx sensor to be modified so as to generate a "platinum-zirconia mixed region", thereby increasing a reaction interface amount. In addition, in accordance with increase in the interface amount, oxygen 1100 adsorbed on the electrode 1002 also increases. Meanwhile, an outer pump electrode (Ip1+electrode) 1004 is not subjected to the rich aging treatment, and thus less oxygen 1100 is adsorbed on the electrode 1004.

However, when the measurement atmosphere has changed from lean to rich and rich gas 1200 reaches the outer pump electrode 1004, the oxygen 1100 adsorbed on the outer pump electrode 1004 is consumed by the rich gas 1200, and the oxygen partial pressure at the outer pump electrode 1004 abruptly decreases. Meanwhile, since more oxygen 1100 is adsorbed on the inner pump electrode 1002 than on the outer pump electrode 1004, even when rich gas 1200 reaches the inner pump electrode 1002, oxygen remains on the inner pump electrode 1002, and the amount of reduction in the oxygen partial pressure at the inner pump electrode 1002 is small.

Therefore, electromotive force indicated by the arrow in FIG. 6 is generated between the inner pump electrode 1002 and the outer pump electrode 1004 which are different from each other in oxygen partial pressure, and current transiently flows in the first pump cell. Accordingly, a noise peak indicated by the solid line in FIG. 7 may be generated, and detection accuracy may decrease.

The present invention has been made in view of such circumstances, and an object of the present invention is to provide a NOx sensor element and a NOx sensor in which: noise current in a first pump cell caused when a measurement atmosphere has changed is suppressed; and reduction in detection accuracy is suppressed.

SUMMARY OF THE INVENTION

Means for Solving the Problems

In order to solve the above-described problems, a NOx sensor element of the present invention includes: a first pump cell configured to pump out and pump in oxygen in a measurement target gas introduced into a first measurement chamber, to adjust an oxygen concentration in the first measurement chamber; a diffusion resistance portion disposed between outside and the first measurement chamber and configured to adjust a diffusion rate of the measurement target gas introduced into the first measurement chamber; and a second pump cell in which a pump current corresponding to a NOx concentration in the measurement target gas after the adjustment of the oxygen concentration flows. The first pump cell includes: a first solid electrolyte; an inner pump electrode containing a noble metal, formed on a surface of the first solid electrolyte, and exposed to the first measurement chamber; and an outer pump electrode containing a noble metal, formed on a surface of the first solid electrolyte, and disposed outside the first measurement chamber. The outer pump electrode contains not less than 22% by mass of a main component of the first solid electrolyte.

According to the NOx sensor element, at least the outer pump electrode contains not less than 22% by mass of the main component of the first solid electrolyte layer. Thus, when a rich aging treatment is performed, modification of the outer pump electrode is accelerated, and more oxygen is adsorbed on the outer pump electrode.

As a result, when a rich aging treatment is performed also on the inner pump electrode, the amount of oxygen adsorbed on the inner pump electrode and the amount of oxygen adsorbed on the outer pump electrode become approximately equal to each other. Accordingly, even when the measurement atmosphere has changed from lean to rich, the amounts of reductions in the oxygen partial pressures on both electrodes are small, and electromotive force due to the difference in oxygen partial pressure between both electrodes decreases. Thus, noise current flowing to the first pump cell decreases, and reduction in detection accuracy can be suppressed.

In the NOx sensor element of the present invention, the inner pump electrode may contain not less than 22% by mass of the main component of the first solid electrolyte.

According to the NOx sensor element, when a rich aging treatment is performed, modification of the inner pump electrode is accelerated, and the amount of oxygen adsorbed on the inner pump electrode and the amount of oxygen adsorbed on the outer pump electrode become more approximately equal to each other.

In the NOx sensor element of the present invention, the outer pump electrode may contain not less than 26% by mass of the main component of the first solid electrolyte.

According to the NOx sensor element, when a rich aging treatment is performed, modification of the outer pump electrode is more accelerated, and the amount of oxygen adsorbed on the outer pump electrode further increases.

In the NOx sensor element of the present invention, a surface of the outer pump electrode, that is oriented toward the outside may be covered by a porous protection layer.

The present invention is applicable also to such a NOx sensor element.

A NOx sensor of the present invention includes: the NOx sensor element; and a metal shell configured to hold the NOx sensor element.

Effects of the Invention

According to the present invention, it is possible to obtain a NOx sensor element in which noise current in the first pump cell caused when the measurement atmosphere has changed is suppressed, and reduction in detection accuracy is suppressed.

DETAILED DESCRIPTION OF THE INVENTION

Hereinafter, embodiments of the present invention will be described with reference to the drawings.

A NOx sensor 1 according to the embodiment of the present invention is a gas sensor to be mounted to an exhaust pipe in automobiles and various internal combustion engines. The NOx sensor 1 is configured by assembling a NOx sensor element (detection element) 100 for detecting a specific gas (nitrogen oxide: NOx) in measurement target exhaust gas.

Figure 1:
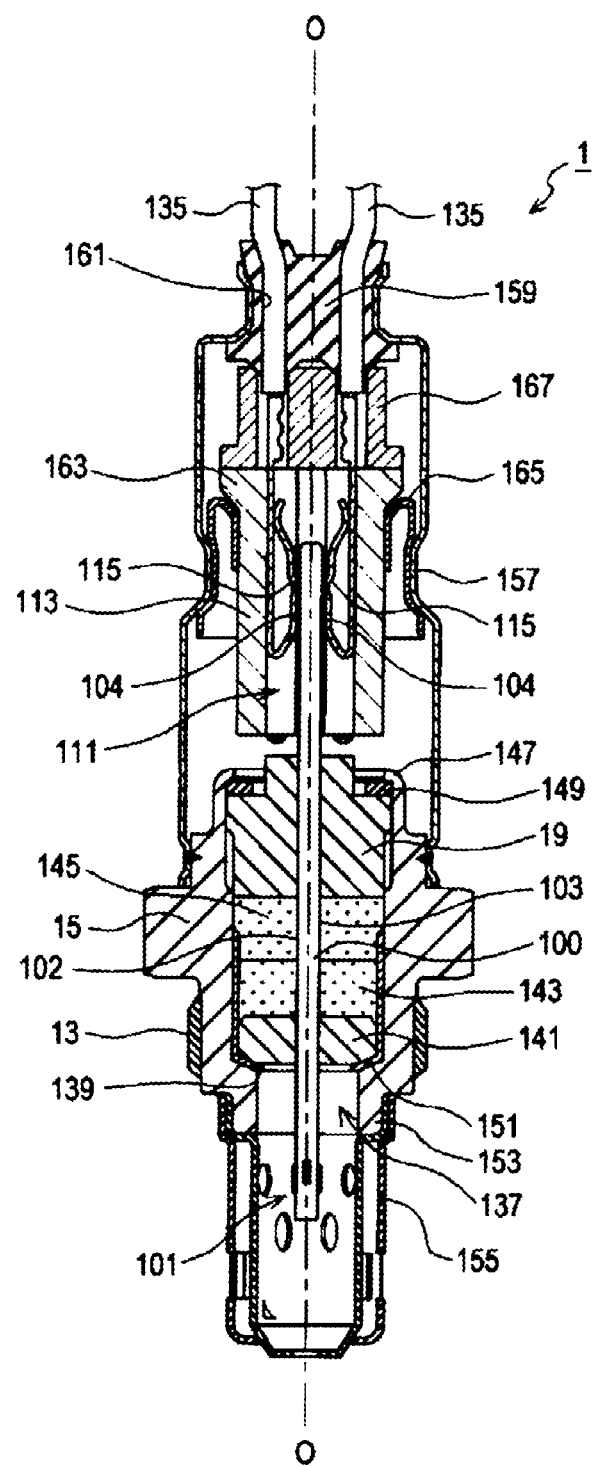
FIG. 1 is a cross-sectional view along the longitudinal direction of a NOx sensor.

As shown in FIG. 1, the NOx sensor 1 includes: a tubular metal shell 15 having a screw portion 13, for fixation to the exhaust pipe, formed on the outer surface of the metal shell 15; a plate-shaped NOx sensor element 100 extending in the direction of an axial line O (the longitudinal direction of the NOx sensor 1: the up-down direction in FIG. 1); a tubular ceramic sleeve 19 disposed so as to surround the periphery of the NOx sensor element 100; a first separator 113 disposed in a state where the inner wall surface of an insertion hole 111 penetrating the first separator 113 in the direction of the axial line O surrounds the periphery of a rear end portion of the NOx sensor element 100; and six connection terminals 115 (only two of the six are shown in FIG. 1) disposed between the NOx sensor element 100 and the first separator 113.

The NOx sensor element 100 is formed in a rectangular parallelepiped shape (plate shape) extending in the longitudinal direction, and has, on a front side thereof, a detection portion 101 which detects a specific gas (here, NOx) contained in a measurement target gas. In the NOx sensor element 100, three electrode pads 104 are formed on each of a first main surface 102 and a second main surface 103 of the outer surface on the rear side (the upper side of FIG. 1: a rear end portion in the longitudinal direction) (not shown in detail). The first main surface 102 and the second main surface 103 are in a positional relationship of opposite surfaces.

The different connection terminals 115 are electrically connected to the six electrode pads 104 of the NOx sensor element 100, respectively. The connection terminals 115 are electrically connected to lead wires 135 arranged in the sensor from the outside. Accordingly, current paths for current flowing between the electrode pads 104 and an external device to which the lead wires 135 are connected, are formed.

The metal shell 15 has a through-hole 137 penetrating the metal shell 15 in the direction of the axial line O, and is formed in a substantially tubular shape having a ledge portion 139 projecting inward in the radial direction of the through-hole 137. The metal shell 15 is configured to hold the NOx sensor element 100 inserted in the through-hole 137, in a state where the detection portion 101 of the NOx sensor element 100 is disposed on the front side relative to the front end of the through-hole 137 and the six electrode pads 104 are disposed on a rear side relative to the rear end of the through-hole 137.

In the through-hole 137 of the metal shell 15, a ceramic holder 141, talc rings 143 and 145, and the ceramic sleeve 19 which are annular are stacked in this order from the front side to the rear side in a state of surrounding the periphery of the NOx sensor element 100. A crimping packing 149 is disposed between the ceramic sleeve 19 and a rear end portion 147 of the metal shell 15. The rear end portion 147 of the metal shell 15 is crimped via the crimping packing 149 so as to press the ceramic sleeve 19 frontward. A metal holder 151 which holds the talc rings 143 and 145 and the ceramic holder 141 is disposed between the ceramic holder 141 and the ledge portion 139 of the metal shell 15.

A double-structure protector 155 made of metal (for example, stainless steel or the like) and covering a projecting portion of the NOx sensor element 100 is attached by welding or the like to the outer periphery of a front end portion 153 of the metal shell 15. An outer casing 157 is fixed to the rear-side outer periphery of the metal shell 15. A grommet 159 having six lead wire insertion holes 161 (only two of the six are shown in FIG. 1) formed therein is disposed in a rear-side opening of the outer casing 157. The six lead wires 135 (two of the six are shown in FIG. 1) electrically connected to the six electrode pads 104, respectively, are inserted in the six lead wire insertion holes 161.

A flange portion 163 is formed at the outer periphery of the first separator 113. The flange portion 163 is fixed to the outer casing 157 via a holding member 165. A second separator 167 held between the first separator 113 and the grommet 159 is disposed on the rear side relative to the first separator 113. The rear side of each connection terminal 115 is inserted in the second separator 167.

Next, a configuration of the NOx sensor element 100 will be described.

Figure 2:
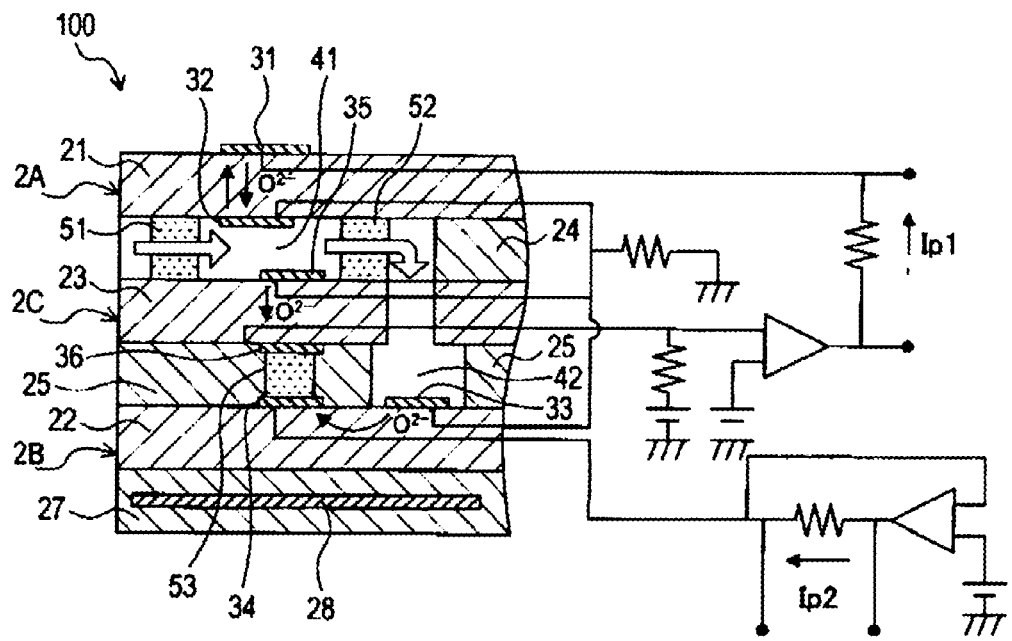
FIG. 2 is a cross-sectional view along the longitudinal direction of a NOx sensor element.

As shown in FIG. 2, the NOx sensor element 100 has a structure in which a first solid electrolyte layer (first solid electrolyte) 21, an insulation layer 24, a third solid electrolyte layer 23, an insulation layer 25, a second solid electrolyte layer (second solid electrolyte) 22, and an insulation layer 27 are stacked in this order. The insulation layer 24 is cut into a U shape toward the front end of the NOx sensor element 100, and the cut portion forms a first measurement chamber 41. A measurement target gas is introduced from the outside through a first diffusion resistor (diffusion resistance portion) 51 disposed at the front end (inlet) of the first measurement chamber 41 into the first measurement chamber 41.

A first pump cell 2A includes: the first solid electrolyte layer 21 formed from zirconia having oxygen ion conductivity as a main material (the proportion thereof exceeds 50% by mass of the entirety); and a pair of electrodes 31 and 32 disposed so as to hold therebetween the first solid electrolyte layer 21. The inner pump electrode 32 faces the first measurement chamber 41 and functions as an Ip1− electrode. The outer pump electrode 31 faces the outside and functions as an Ip1+electrode. Each of the electrodes 31 and 32 contains a noble metal. In this example, each of the electrodes 31 and 32 is formed from platinum as a main material (the proportion thereof exceeds 50% by mass of the electrode).

A second diffusion resistor 52 is disposed at an end, of the first measurement chamber 41, that is opposite to the inlet. A NOx measurement chamber (second measurement chamber) 42 which is in communication with the first measurement chamber 41 is formed on the further inside relative to the first measurement chamber 41 with the second diffusion resistor 52 interposed therebetween. The NOx measurement chamber 42 is formed between the first solid electrolyte layer 21 and the second solid electrolyte layer 22 so as to penetrate the third solid electrolyte layer 23.

A second pump cell 2B includes: the second solid electrolyte layer 22 formed from zirconia having oxygen ion conductivity as a main material; and a pair of second electrodes 33 and 34. One of the second electrodes, i.e., the second electrode 33, is disposed on a surface, of the second solid electrolyte layer 22, that faces the NOx measurement chamber 42. The other second electrode 34 functions as a counter electrode for the second electrode 33 and is disposed outside the NOx measurement chamber 42. Each of the second electrodes 33 and 34 is formed from platinum as a main material. The second electrode 34 is disposed, on the second solid electrolyte layer 22, in a cut portion of the insulation layer 25, and faces a reference oxygen chamber 53 so as to oppose a reference electrode 36 described later.

An oxygen concentration detection cell 2C includes: the third solid electrolyte layer 23 formed from zirconia having oxygen ion conductivity as a main material; and a detection electrode 35 and the reference electrode 36 disposed so as to hold therebetween the third solid electrolyte layer 23. The detection electrode 35 is located on the downstream side relative to the inner pump electrode 32 and faces the first measurement chamber 41. Each of the detection electrode 35 and the reference electrode 36 is formed from platinum as a main material. Although not shown, the end edge of the detection electrode 35 is held in the stacking direction by an insulation coat layer formed from alumina as a main material.

The insulation layer 25 is cut such that the reference electrode 36 in contact with the third solid electrolyte layer 23 is disposed therein. The cut portion is filled with a porous body and forms the reference oxygen chamber 53. Weak current having a predetermined value is caused to flow in the oxygen concentration detection cell 2C in advance, to send oxygen from the first measurement chamber 41 into the reference oxygen chamber 53, whereby an oxygen reference is obtained.

A heater 28 extending along the longitudinal direction of the NOx sensor element 100 is embedded in the insulation layer 27. The heater 28 is used for increasing the temperature of the NOx sensor element 100 to an activation temperature so as to improve the oxygen ion conductivity of each solid electrolyte layer (the first solid electrolyte layer 21, the second solid electrolyte layer 22, and the third solid electrolyte layer 23), thereby stabilizing operation. Each of the insulation layers 24, 25, and 27 is formed from alumina as a main material. Each of the first diffusion resistor 51 and the second diffusion resistor 52 is formed from a porous substance such as alumina. The heater 28 is formed from platinum or the like.

Next, an example of the operation of the NOx sensor element 100 will be described.

First, when the first pump cell 2A, the second pump cell 2B, and the oxygen concentration detection cell 2C are each heated to an activation temperature (for example, 550° C. or higher) by the heater 28, excessive oxygen in a measurement target gas (exhaust gas) having flowed into the first measurement chamber 41 is pumped out by the first pump cell 2A from the inner pump electrode 32 toward the outer pump electrode 31.

At this time, a first pump current Ip1 corresponding to the oxygen concentration in the measurement target gas flows in the first pump cell 2A. The oxygen concentration in the first measurement chamber 41 corresponds to a voltage between the electrodes of the oxygen concentration detection cell 2C. Thus, the flow amount of the first pump current Ip1 is controlled such that the voltage between the electrodes becomes a constant voltage (for example, 425 mV), thereby adjusting the oxygen concentration in the first measurement chamber 41 to such a predetermined concentration that NOx is not decomposed.

The measurement target gas having been subjected to the adjustment of the oxygen concentration further flows toward the NOx measurement chamber 42. At this time, a constant voltage (a voltage having a value higher than the value of a control voltage of the oxygen concentration detection cell 2C; for example, 450 mV) that would cause NOx gas in the measurement target gas to be decomposed into nitrogen ($N_2$) and oxygen ($O_2$), is applied as a voltage between terminals (a voltage between the electrodes) of the second pump cell 2B, whereby NOx is decomposed into nitrogen and oxygen.

Then, a second pump current Ip2 flows in the second pump cell 2B such that the oxygen generated by the decomposition of the NOx is pumped out from the NOx measurement chamber 42 toward the second electrode 34 disposed in the reference oxygen chamber 53. A linear relationship is present between the second pump current Ip2 and the NOx concentration, and thus, if the second pump current Ip2 is detected, the NOx concentration in the measurement target gas can be detected.

As described above, in the NOx sensor 1, the second pump current Ip2 is detected and converted into a NOx concentration (in the present embodiment, a value obtained by conversion into a nitrogen oxide concentration is described, and thus conversion into a NOx concentration is described, but, to be exact, NO concentration conversion is performed), whereby the NOx concentration can be detected.

In the present embodiment, a NOx concentration-converted value based on the second pump current Ip2 can be calculated by a microcomputer (not shown), which is connected to the NOx sensor element 100, converting the second pump current Ip2 into a voltage, reading the voltage, and calculating a NOx concentration with use of a predetermined computing equation or the like.

Next, the inner pump electrode 32 and the outer pump electrode 31 will be described.

In the NOx sensor of the present embodiment, the NOx sensor element 100 is heated to a predetermined temperature region, and positive voltage is applied between the electrodes 31 and 32 in a rich atmosphere, whereby a first rich aging treatment of applying voltage between the electrodes 31 and 32 is performed such that the first pump cell 2A pumps out oxygen from the first measurement chamber 41.

Figure 3:
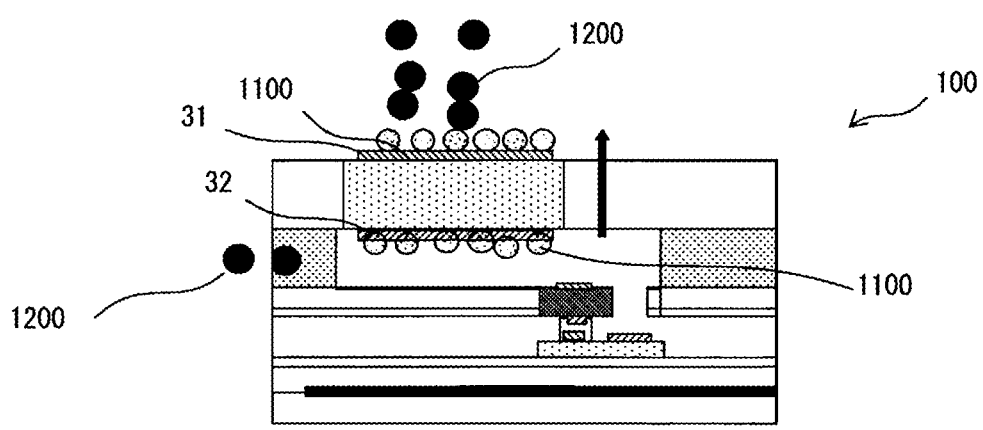
FIG. 3 is a diagram showing, with respect to an inner pump electrode and an outer pump electrode after a rich aging treatment, oxygen on the electrodes adsorbed when a measurement atmosphere has changed from lean to rich.

Accordingly, as shown in FIG. 3, a part of the inner pump electrode 32 is modified so as to generate a "platinum-zirconia mixed region", thereby increasing a reaction interface amount. In addition, in accordance with increase in the interface amount, oxygen 1100 adsorbed on the inner pump electrode 32 also increases.

Next, negative voltage is applied between the electrodes 31 and 32, whereby a second rich aging treatment of applying voltage between the electrodes 31 and 32 is performed such that the first pump cell 2A pumps in oxygen to the first measurement chamber 41.

Accordingly, as shown in FIG. 3, a part of the outer pump electrode 31 is modified so as to generate a "platinum-zirconia mixed region", thereby increasing the reaction interface amount. In addition, in accordance with increase in the interface amount, oxygen 1100 adsorbed on the outer pump electrode 31 also increases.

Here, at least the outer pump electrode 31 contains not less than 22% by mass, and preferably not less than 26% by mass, of a main component of the first solid electrolyte layer 21. Accordingly, modification of the outer pump electrode 31 by the rich aging treatment is accelerated and more oxygen 1100 is adsorbed on the outer pump electrode 31.

The reason why the outer pump electrode 31 is formed so as to contain the main component of the first solid electrolyte layer 21 is as follows. Since an outside measurement target gas comes into contact with the inner pump electrode 32 via the first diffusion resistor 51, even when the measurement atmosphere has changed from lean to rich, the rich atmosphere is less likely to reach the surface of the inner pump electrode 32, and thus influence, on the oxygen partial pressure, of the change in the atmosphere is less at the inner pump electrode 32 than at the outer pump electrode 31. As a matter of course, it is preferable that the inner pump electrode 32 also contains not less than 22% by mass of the main component of the first solid electrolyte layer 21.

As described above, at least the outer pump electrode 31 contains not less than 22% by mass of the main component of the first solid electrolyte layer 21. Thus, even when the measurement atmosphere has changed from lean to rich and rich gas 1200 reaches each of the inner pump electrode 32 and the outer pump electrode 31, since much oxygen 1100 is adsorbed on each of the electrodes 31 and 32, oxygen remains both on the electrodes 31 and 32 in the same manner, and the amount of reduction in the oxygen partial pressure at each of the electrodes 31 and 32 is small.

Therefore, as indicated by the arrow in FIG. 3, electromotive force due to the difference in oxygen partial pressure between the inner pump electrode 32 and the outer pump electrode 31 is low. In addition, as indicated by the broken line in FIG. 7, noise current flowing in the first pump cell decreases, and reduction in detection accuracy can be suppressed.

Here, the "rich atmosphere" means an atmosphere in which the ratio of oxygen is low in comparison to a stoichiometric air/fuel ratio ($\lambda=1$). That is, the "rich atmosphere" means a gas atmosphere in which the ratio of oxygen is lower (the oxygen partial pressure is lower) than in a reference gas atmosphere obtained by combustion at the stoichiometric air/fuel ratio which is an air/fuel mixture ratio that enables ideal complete combustion.

As the method for applying positive voltage and negative voltage between the electrodes 31 and 32, a method using alternating voltage may be employed. Alternatively, a method may be employed in which, first, a rich aging treatment is performed on one of the electrodes with either one of polarities and finished, and then a rich aging treatment is performed on the other electrode with the opposite polarity.

Alternatively, while an aging treatment is being performed on the first pump cell 2A, an aging treatment may be performed also on the second pump cell 2B, as appropriate.

It is needless to say that the present invention is not limited to the above-described embodiment at all and the present invention can be carried out in various modes without departing from the scope of the present invention.

In the above-described embodiment, the NOx sensor 1 is applied to a gas sensor for detecting the NOx gas concentration in exhaust gas in automobiles and various internal combustion engines. However, the NOx sensor 1 is also applicable to, for example, a gas sensor for detecting the NOx gas concentration in combustion gas in a boiler or the like.

Figures 4, 5:
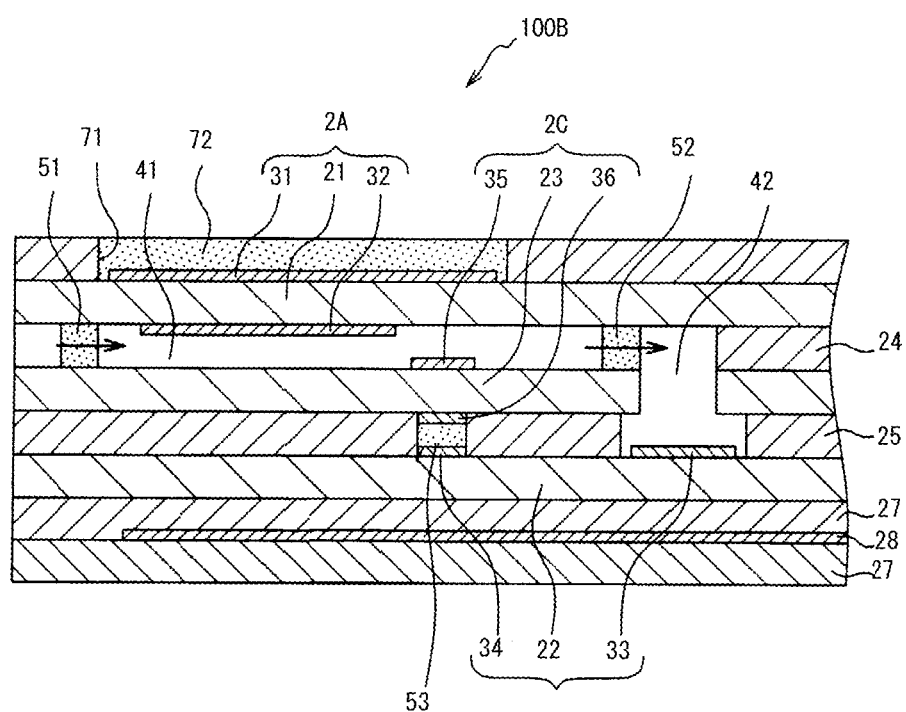
FIG. 4 is a cross-sectional view along the longitudinal direction of a NOx sensor element of another embodiment of the present invention.
FIG. 5 is a diagram describing the magnitude of noise current that flowed in a first pump cell when the measurement atmosphere was changed from lean to rich at changed proportions of a main component of a first solid electrolyte, contained in the outer pump electrode.
Figure 6:
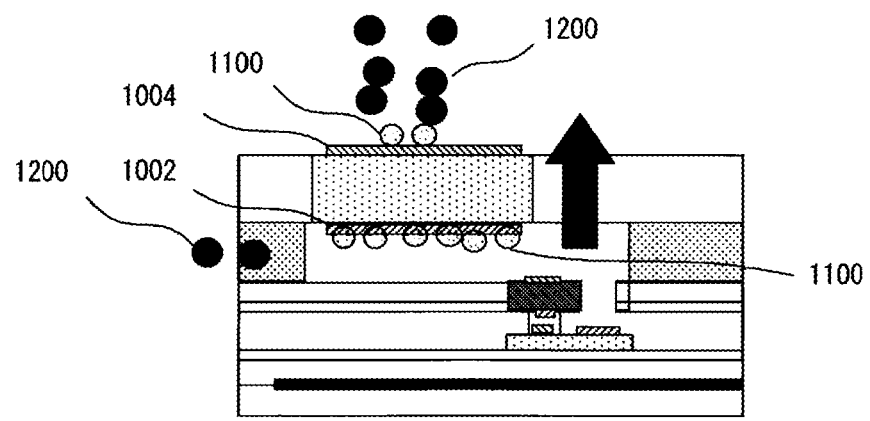
FIG. 6 is a diagram showing oxygen on electrodes adsorbed when the measurement atmosphere has changed from lean to rich after an inner pump electrode of a conventional NOx sensor is subjected to a rich aging treatment.

In the above-described embodiment, the outer pump electrode 31 is exposed on the outer surface of the NOx sensor element 100. However, as shown in FIG. 4, the outer pump electrode 31 may be covered by a porous protection layer 72 so that an outside measurement target gas comes into contact with the outer pump electrode 31 via the porous protection layer 72. In a NOx sensor element 100B in FIG. 4, the same components as those in the NOx sensor element 100 are denoted by the same reference characters, and description thereof is omitted. The porous protection layer 72 has a substantially rectangular shape and is embedded in a front-side rectangular opening of an outer insulation layer 71. The outer insulation layer 71 covers the first solid electrolyte layer 21.

In addition, in the above-described embodiment, the solid electrolyte layers forming the NOx sensor element 100 are three layers which are the first solid electrolyte layer 21, the second solid electrolyte layer 22, and the third solid electrolyte layer 23. However, the solid electrolyte layers forming the NOx sensor element 100 may be, for example, two layers which are the first solid electrolyte layer 21 and the second solid electrolyte layer 22.

In addition, in the above-described embodiment, the NOx sensor element 100 is configured such that one of the electrodes of the first pump cell 2A (inner pump electrode 32) faces the first measurement chamber 41 and one of the electrodes of the second pump cell 2B (second electrode 33) faces the NOx measurement chamber 42 which is different from the first measurement chamber. However, the NOx sensor element 100 may be configured such that both electrodes 32 and 33 of the first pump cell 2A and the second pump cell 2B face a common chamber (first measurement chamber 41).

EXAMPLES

Experimental Example 1

NOx sensor elements 100 and NOx sensors 1 shown in FIG. 1 and FIG. 2 were manufactured. Each NOx sensor element 100 was heated to 800 to 850° C., and positive voltage and negative voltage were applied between the electrodes 31 and 32 by means of alternating voltage in a rich atmosphere (composition, $H_2$: 3% by volume, water ($H_2O$): 10% by volume, $N_2$: remainder), whereby rich aging treatments were performed on the electrodes 31 and 32.

The proportions of a main component, of the first solid electrolyte 21, contained in the outer pump electrode 31 were set to be 14% by mass and 22% by mass, respectively.

Figure 7:
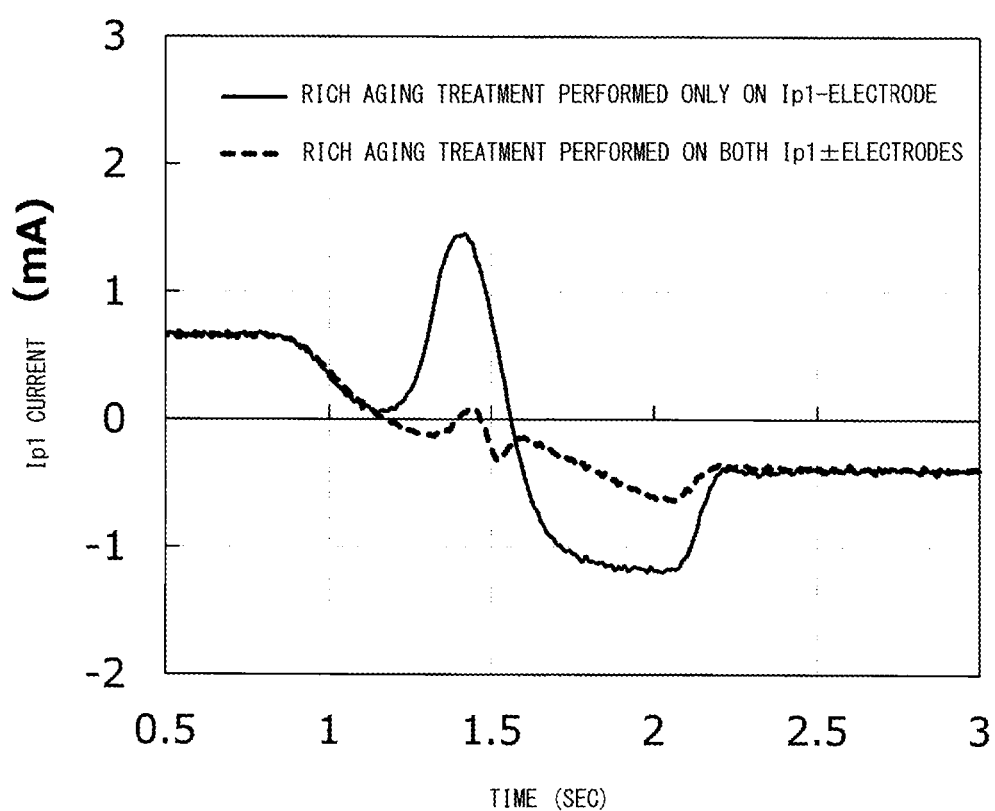
FIG. 7 is a diagram showing noise current in the first pump cell caused when the measurement atmosphere was changed from lean to rich.

Evaluations were made in comparison to the height of the positive noise peak of an Ip1 current that is indicated by the solid line in FIG. 7 and that flowed when rich aging was performed only on the inner pump electrode 32 (Ip-electrode). Specifically, if the height of the noise peak was not greater than ½ the aforementioned height, the evaluation "good (○)" was made. Meanwhile, if the height of the noise peak was greater than ½ the aforementioned height, the evaluation "not good (x)" was made.

The obtained results are shown in FIG. 5.

In the case where the proportion of the main component, of the first solid electrolyte 21, contained in the outer pump electrode 31 was 22% by mass, even when the measurement atmosphere was changed from lean to rich, electromotive force between the electrodes 31 and 32 was low, and noise current flowing in the first pump cell was low.

Meanwhile, in the case where the proportion of the main component, of the first solid electrolyte 21, contained in the outer pump electrode 31 was 14% by mass, noise current was higher than in the case where the proportion was 22% by mass.

Experimental Example 2

Next, rich aging treatments were performed as in Experimental example 1 on NOx sensor elements 100 and NOx sensors 1 that had the same structures as those in Experimental example 1 and that had dimensions and element thicknesses different from those in Experimental example 1. In addition, noise current in the first pump cell caused when the measurement atmosphere was changed from lean to rich, was measured in the same manner.

Experimental example 2 was performed to check effects obtained when the proportions of the main component, of the first solid electrolyte 21, contained in the outer pump electrode 31 were set to be 22% by mass and 26% by mass, respectively. Since the NOx sensor elements in Experimental example 2 had dimensions and the like different from those in Experimental example 1, numerical values cannot be simply compared to the Ip1 currents in FIG. 7 in Experimental example 1.

Figure 8:
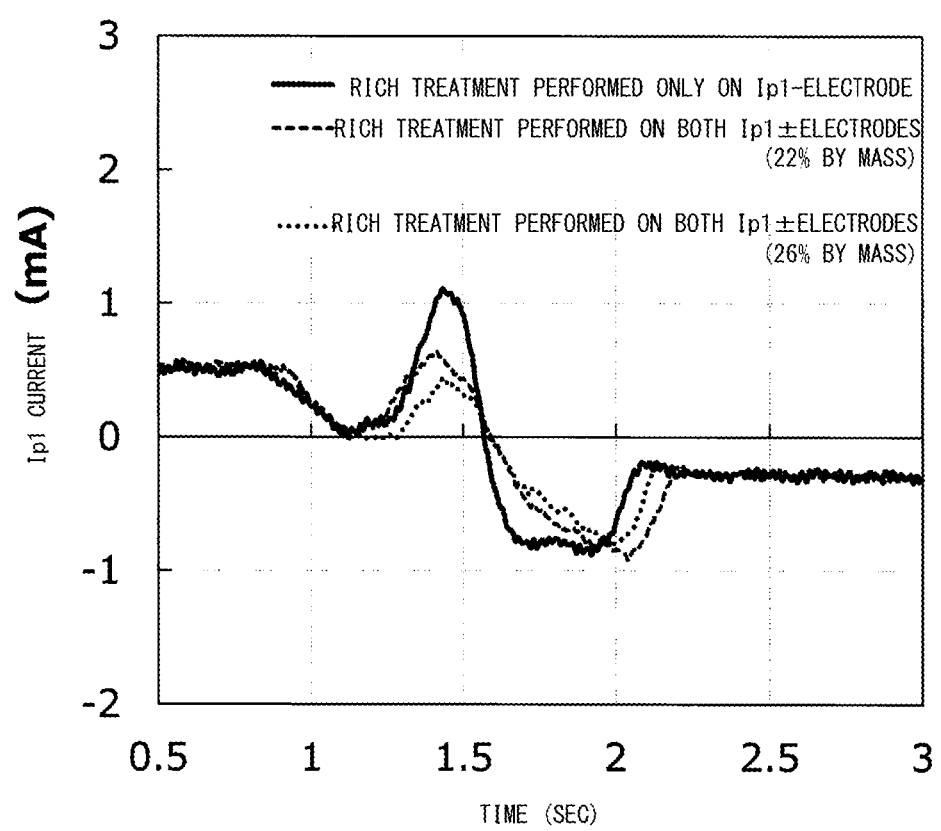
FIG. 8 is a diagram showing noise current in the first pump cell caused when the measurement atmosphere was changed from lean to rich in Experimental example 2.

FIG. 8 is a diagram showing noise current in the first pump cell caused when the measurement atmosphere was changed from lean to rich in Experimental example 2. The current when the rich aging was performed only on the inner pump electrode 32 (Ip-electrode), is indicated by a solid line.

In the case where the proportion of the main component, of the first solid electrolyte 21, contained in the outer pump electrode 31 was 22% by mass, even when the measurement atmosphere was changed from lean to rich, electromotive force between the electrodes 31 and 32 was low and noise current flowing in the first pump cell was also low, as compared to the height of the positive noise peak of the Ip1 current when the rich aging was performed only on the inner pump electrode 32 (Ip-electrode).

In the case where the proportion of the main component, of the first solid electrolyte 21, contained in the outer pump electrode 31 was 26% by mass, the noise current was further lower than in the case where the proportion was 22% by mass.

Therefore, it is found to be more preferable that the outer pump electrode contains not less than 26% by mass of the main component of the first solid electrolyte. However, if the proportion of the main component, of the first solid electrolyte 21, contained in the outer pump electrode 31 is excessively high, the internal resistance of the Ip1 cell increases, oxygen leaking to the NOx measurement chamber increases, and reduction in the measurement accuracy or the like may occur. Thus, the upper limit for the proportion is considered to be about 50% by mass.

DESCRIPTION OF REFERENCE NUMERALS

1: NOx sensor
2A: first pump cell
2B: second pump cell
15: metal shell
21: first solid electrolyte layer (first solid electrolyte)
31: outer pump electrode
32: inner pump electrode
41: first measurement chamber
51: first diffusion resistor (diffusion resistance portion)
72: porous protection layer
100: NOx sensor element

The invention claimed is:
1. A NOx sensor element comprising:
   a first pump cell configured to pump out and pump in oxygen in a measurement target gas introduced into a first measurement chamber, to adjust an oxygen concentration in the first measurement chamber;
   a diffusion resistance portion disposed between outside and the first measurement chamber and configured to adjust a diffusion rate of the measurement target gas introduced into the first measurement chamber; and
   a second pump cell in which a pump current corresponding to a NOx concentration in the measurement target gas after the adjustment of the oxygen concentration flows, wherein
   the first pump cell includes;
   a first solid electrolyte, an inner pump electrode containing a noble metal, formed on a surface of the first solid electrolyte, and exposed to the first measurement chamber, and an outer pump electrode containing a noble metal, formed on a surface of the first solid electrolyte, and disposed outside the first measurement chamber, and the outer pump electrode contains not less than 22% by mass of a main component of the first solid electrolyte.

2. The NOx sensor element according to claim 1, wherein the inner pump electrode contains not less than 22% by mass of the main component of the first solid electrolyte.

3. The NOx sensor element according to claim 1, wherein the outer pump electrode contains not less than 26% by mass of the main component of the first solid electrolyte.

4. The NOx sensor element according to claim 1, wherein a surface of the outer pump electrode, that is oriented toward the outside is covered by a porous protection layer.

5. A NOx sensor comprising:

the NOx sensor element according to claim 1; and a metal shell configured to hold the NOx sensor element.

6. The NOx sensor element according to claim 1, wherein an outer surface of the outer pump electrode is entirely exposed to the outside.

7. The NOx sensor element according to claim 1, wherein the inner pump electrode and the outer pump electrode are provided such that an amount of oxygen adsorbed on the inner pump electrode and an amount of oxygen adsorbed on the outer pump electrode become approximately equal to each other when the measurement target gas has changed from lean to rich.

8. The NOx sensor element according to claim 1, wherein the main component of the first solid electrolyte is zirconia having oxygen ion conductivity.

9. The NOx sensor element according to claim 8, wherein the first solid electrolyte contains zirconia in an amount of more than 50% by mass.

10. The NOx sensor element according to claim 8, wherein the outer pump electrode contains platinum as a main material and has a platinum-zirconia region where more oxygen is absorbed on an outer surface of the outer pump electrode.

* * * * *